(12) United States Patent
Han et al.

(10) Patent No.: US 10,987,522 B2
(45) Date of Patent: Apr. 27, 2021

(54) THREE DIMENSIONAL LOCALIZATION AND TRACKING FOR ADAPTIVE RADIATION THERAPY

(71) Applicant: Elekta, Inc., Atlanta, GA (US)

(72) Inventors: Xiao Han, Chesterfield, MO (US); Yan Zhou, Saint Peters, MO (US)

(73) Assignee: Elekta, Inc., Atlanta, GA (US)

( * ) Notice: Subject to any disclaimer, the term of this patent is extended or adjusted under 35 U.S.C. 154(b) by 181 days.

(21) Appl. No.: 16/218,404

(22) Filed: Dec. 12, 2018

(65) Prior Publication Data

US 2019/0117998 A1   Apr. 25, 2019

Related U.S. Application Data

(63) Continuation of application No. 15/852,860, filed on Dec. 22, 2017, now Pat. No. 10,188,874, which is a
(Continued)

(51) Int. Cl.
*G06K 9/00* (2006.01)
*A61N 5/10* (2006.01)
*G06T 7/246* (2017.01)

(52) U.S. Cl.
CPC ......... *A61N 5/1037* (2013.01); *A61N 5/1049* (2013.01); *G06T 7/246* (2017.01);
(Continued)

(58) Field of Classification Search
None
See application file for complete search history.

(56) References Cited

U.S. PATENT DOCUMENTS 9,878,177 B2   1/2018   Han et al.
10,188,874 B2   1/2019   Han et al.
(Continued)

FOREIGN PATENT DOCUMENTS

AU   2016211816 A1   8/2017
AU   2016211816 B2   9/2018
(Continued)

OTHER PUBLICATIONS

"Chinese Application Serial No. 201680014207.1, Office Action dated May 27, 2019", w English translation, 11 pgs.
(Continued)

*Primary Examiner* — Atiba O Fitzpatrick
(74) *Attorney, Agent, or Firm* — Schwegman Lundberg & Woessner, P.A.; Sanjay Agrawal

(57) ABSTRACT

The present disclosure relates to systems, methods, and computer-readable storage media for segmenting medical image. Embodiments of the present disclosure may locate and track a moving, three-dimensional (3D) target in a patient undergoing image-guided radiation therapy. For example, an adaptive filter model for a region of interest in the patient may be received, wherein the adaptive filter model is based on the target to be tracked. An image acquisition device may obtain a two-dimensional (2D) slice of a region of interest in the patient. A processor may then apply the adaptive filter model to the 2D slice, wherein the adaptive filter model includes an offset value. The processor may also determine a location of the target in the 2D slice based on the adaptive filter model. The processor may also estimate a potential location of the target based on the offset value. The processor may then repeat one or more of the above steps to track the moving target during image-guided radiation therapy of the patient.

20 Claims, 6 Drawing Sheets

Related U.S. Application Data continuation of application No. 14/607,654, filed on Jan. 28, 2015, now Pat. No. 9,878,177.

(52) U.S. Cl.
CPC .... *A61N 5/1039* (2013.01); *A61N 2005/1055* (2013.01); *G06T 2207/10081* (2013.01); *G06T 2207/10088* (2013.01); *G06T 2207/30096* (2013.01)

(56) References Cited

U.S. PATENT DOCUMENTS

| | | |
|---|---|---|
| 2008/0159478 A1 | 7/2008 | Keall et al. |
| 2008/0317314 A1* | 12/2008 | Schwartz ............... G06K 9/34 382/131 |
| 2009/0034819 A1 | 2/2009 | Nord et al. |
| 2012/0063656 A1 | 3/2012 | Jao et al. |
| 2012/0071758 A1 | 3/2012 | Lachaine et al. |
| 2014/0055135 A1 | 2/2014 | Nielsen et al. |
| 2014/0107390 A1 | 4/2014 | Brown et al. |
| 2014/0275705 A1 | 9/2014 | Virshup et al. |
| 2016/0213947 A1 | 7/2016 | Han et al. |
| 2018/0133510 A1 | 5/2018 | Han et al. |

FOREIGN PATENT DOCUMENTS

| | | |
|---|---|---|
| CN | 101553281 | 10/2009 |
| EP | 3250288 A1 | 12/2017 |
| JP | 2006304818 | 11/2006 |
| JP | 2007517610 A | 7/2007 |
| JP | 2010517655 A | 5/2010 |
| JP | 2012024145 | 2/2012 |
| JP | 2012210232 | 11/2012 |
| JP | 2012254243 | 12/2012 |
| JP | 2013202242 A | 10/2013 |
| WO | 2005030330 | 4/2005 |
| WO | 2011133606 | 10/2011 |
| WO | WO-2014018983 A1 | 1/2014 |
| WO | WO-2016122957 A1 | 8/2016 |

OTHER PUBLICATIONS

"Russian Application Serial No. 2017130142, Office Action dated Jun. 4, 2019", w English translation, 9 pgs.

"Russian Application Serial No. 2017130142, Response filed Aug. 22, 2019 to Office Action dated Jun. 4, 2019", w o English claims, 3 pgs.

Chernyy, S A, "Frequency and spatial methods of digital image filtering—Molodozhnyy nauchno-tekhnicheskiy vestnik", w English Translation, (May 5, 2012), 14 pgs.

"Chinese Application Serial No. 201680014207.1, Response filed Oct. 11, 2019 to Office Action dated May 27, 2019", w o English claims (not amended), 4 pgs.

"Japanese Application Serial No. 2017-540138, Notification of Reasons for Rejection dated Oct. 29, 2019", w English Translation, 4 pgs.

"Japanese Application Serial No. 2017-540138, Response filed Nov. 14, 2019 to Notification of Reasons for Rejection dated Oct. 29, 2019", w English claims, 7 pgs.

"U.S. Appl. No. 14/607,654, Notice of Allowance dated Sep. 22, 2017", 8 pgs.

"U.S. Appl. No. 15/852,860, Non Final Office Action dated May 10, 2018", 5 pgs.

"U.S. Appl. No. 15/852,860, Notice of Allowability dated Oct. 3, 2018", 2 pgs.

"U.S. Appl. No. 15/852,860, Notice of Allowance dated Sep. 12, 2018", 7 pgs.

"U.S. Appl. No. 15/852,860, Preliminary Amendment filed Feb. 9, 2018", 9 pgs.

"U.S. Appl. No. 15/852,860, Response filed Aug. 9, 2018 to Non Final Office Action dated May 10, 2018", 3 pgs.

"Australian Application Serial No. 2016211816, First Examination Report dated May 22, 2018", 3 pgs.

"Australian Application Serial No. 2016211816, Response filed Aug. 18, 2018 to First Examination Report dated May 22, 2018", 9 pgs.

"European Application Serial No. 16702647.5, Response filed Apr. 3, 2018 to Communication pursuant to Rules 161(2) and 162 EPC dated Sep. 22, 2017", 29 pgs.

"International Application Serial No. PCT/US2016/014258, International Preliminary Report on Patentability dated Aug. 10, 2017", 7 pgs.

"International Application Serial No. PCT/US2016/014258, International Search Report dated May 9, 2016", 3 pgs.

"International Application Serial No. PCT/US2016/014258, Written Opinion dated May 9, 2016", 5 pgs.

"Japanese Application Serial No. 2020-000015, Notification of Reasons for Refusal dated Sep. 29, 2020", w/ English Translation, 9 pgs.

"Chinese Application Serial No. 201680014207.1, Office Action dated Mar. 2, 2020", w English Translation, 7 pgs.

"Chinese Application Serial No. 201680014207.1, Response filed Apr. 2, 2020 to Office Action dated Mar. 2, 2020", w English claims, 8 pgs.

"Japanese Application Serial No. 2020-000015, Response filed Dec. 17, 2020 to Notification of Reasons for Refusal dated Sep. 29, 2020", w English claims, 10 pgs.

* cited by examiner

THREE DIMENSIONAL LOCALIZATION AND TRACKING FOR ADAPTIVE RADIATION THERAPY

CROSS-REFERENCE TO RELATED APPLICATION

The present application is a continuation of U.S. application Ser. No. 15/852,860, filed Dec. 22, 2017, which is a continuation of U.S. application Ser. No. 14/607,654, filed Jan. 28, 2015, which is related to U.S. application Ser. No. 14/607,626, filed Jan. 28, 2015 and titled "Three Dimensional Localization of a Moving Target for Adaptive Radiation Therapy," the benefit of priority of each of which is hereby claimed herein, and which applications are hereby incorporated herein by reference in their entirety.

TECHNICAL FIELD

The disclosure generally relates to radiation therapy or radiotherapy. More specifically, this disclosure relates to systems and methods for three-dimensional tracking of a tumor for use in developing a radiation therapy treatment plan to be used during radiotherapy.

BACKGROUND

Radiotherapy is used to treat cancers and other ailments in mammalian (e.g., human and animal) tissue. One such radiotherapy technique is a Gamma Knife, by which a patient is irradiated by a large number of low-intensity gamma rays that converge with high intensity and high precision at a target (e.g., a tumor). In another embodiment, radiotherapy is provided using a linear accelerator, whereby a tumor is irradiated by high-energy particles (e.g., electrons, protons, ions, and the like). The placement and dose of the radiation beam must be accurately controlled to ensure the tumor receives the prescribed radiation, and the placement of the beam should be such as to minimize damage to the surrounding healthy tissue, often called the organ(s) at risk (OARs).

The radiation beam may be shaped to match a shape of the tumor, such as by using a multileaf collimator (e.g., multileaf collimator includes multiple tungsten leaves that may move independently of one another to create customized radiation beam shapes). (Radiation is termed "prescribed" because a physician orders a predefined amount of radiation to the tumor and surrounding organs similar to a prescription for medicine).

Traditionally, for each patient, a radiation therapy treatment plan ("treatment plan") may be created using an optimization technique based on clinical and dosimetric objectives and constraints (e.g., the maximum, minimum, and mean doses of radiation to the tumor and critical organs). The treatment planning procedure may include using a three-dimensional image of the patient to identify a target region (e.g., the tumor) and to identify critical organs near the tumor. Creation of a treatment plan can be a time consuming process where a planner tries to comply with various treatment objectives or constraints (e.g., dose volume histogram (DVH) objectives), taking into account their individual importance (e.g., weighting) in order to produce a treatment plan which is clinically acceptable. This task can be a time-consuming trial-and-error process that is complicated by the various organs at risk (OARs, because as the number of OARs increases (e.g., up to thirteen for a head-and-neck treatment), so does the complexity of the process. OARs distant from a tumor may be easily spared from radiation, while OARs close to or overlapping a target tumor may be difficult to spare.

Computed Tomography (CT) imaging traditionally serves as the primary source of image data for treatment planning for radiation therapy. CT images offer accurate representation of patient geometry, and CT values can be directly converted to electron densities (e.g., Hounsfield units) for radiation dose calculation. However, using CT causes the patient to be exposed to additional radiation dosage. In addition to CT images, magnetic resonance imaging (MRI) scans can be used in radiation therapy due to their superior soft-tissue contrast, as compared to CT images. MRI is free of ionizing radiation and can be used to capture functional information of the human body, such as tissue metabolism and functionality.

Imaging systems such as computed tomography (CT), fluoroscopy, and magnetic resonance imaging (MRI) may be used to determine the location of and track a target (e.g., an organ, a tumor, and the like). MRI is typically used because it provides excellent soft tissue contract without using ionizing radiation as used by CT. An example of a radiotherapy treatment system integrated with an imaging system may include an MRI-Linac, which may use three-dimensional (3D) images of a target (e.g., a tumor). The MRI apparatus of the MRI-Linac may provide a plurality of images that corresponds to a partial map of hydrogen nuclei in tissues of the patient. The patient images may be acquired in a two-dimensional (2D) plane or in a 3D volume. Because organs and tumors move within a patient's body, fast and accurate 3D localization of the target is important. For instance, a target organ or tumor may move because of various types of motion (e.g., respiratory, cardiac, peristalsis or other types of patient motion). However, 2D MR slices are typically acquired at a particular location of the patient's body and the 2D MR slice may not include the tumor/target because of the target organ or tumor motion. Therefore, a system and method to acquire the target tumor and track the structure and motion of the tumor is required such that the acquired 2D MR slice in terms of location, orientation, and/or thickness includes the target tumor and is visible on the 2D MR slices in a clinical environment.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

SUMMARY

Certain embodiments of the present disclosure relate to a method for medical image processing. The method may be implemented by a processor device executing a plurality of computer executable instructions. The method may locate and track a moving, three-dimensional (3D) target in a patient undergoing image-guided radiation therapy, and comprise: (a) receiving an adaptive filter model for a region of interest in the patient, wherein the adaptive filter model is based on the target to be tracked; (b) obtaining, by an image acquisition device, a two-dimensional (2D) slice of a region of interest in the patient; (c) applying, by a processor, the adaptive filter model to the 2D slice, wherein the adaptive filter model includes an offset value; (d) determining, by the processor, a location of the target in the 2D slice based on the adaptive filter model; (e) estimating, by the processor, a potential location of the target based on the offset value; and repeating, by the processor, (b) through (e) to track the moving target during image-guided radiation therapy of the patient.

Certain embodiments of the present disclosure relate to a medical image processing system. The system may locate and track a moving three-dimensional (3D) target to be irradiated using an image-guided radiation therapy device according to a radiation therapy treatment plan, the system may comprise a processor and a memory operatively coupled to the processor. The memory may store a plurality of medical images, a plurality of adaptive filter models, an acquisition protocol, and computer-executable instructions that, when executed by the processor, causes the processor to perform a method. The method may comprise (a) retrieving from memory a two-dimensional (2D) slice according to the acquisition protocol; (b) converting, by the processor, the 2D slice to a particular processing domain; (c) applying, by the processor, the adaptive filter model to the 2D slice, wherein the adaptive filter model includes an offset value; (d) generating, by the processor, a response map for each adaptive filter model, wherein the response map includes a confidence score for each location of the 2D slice; (e) identifying, by the processor, a match between the adaptive filter model and one or more locations on the 2D slice based on a high confidence score; (f) determining, by the processor, a location of the target in the 2D slice based on the high confidence score; (g) estimating, by the processor, a potential location of the target based on the offset value; and retrieving from memory a subsequent 2D MRI slice and repeating (b) through (g) in order to track the moving target during image-guided radiation therapy to the patient.

Additional objects and advantages of the present disclosure will be set forth in part in the following detailed description, and in part will be obvious from the description, or may be learned by practice of the present disclosure. The objects and advantages of the present disclosure will be realized and attained by means of the elements and combinations particularly pointed out in the appended claims.

It is to be understood that the foregoing general description and the following detailed description are exemplary and explanatory only, and are not restrictive of the invention, as claimed.

BRIEF DESCRIPTION OF THE DRAWINGS

In the drawings, which are not necessarily drawn to scale, like numerals may describe similar components in different views. Like numerals having letter suffixes or different letter suffixes may represent different instances of similar components. The drawings illustrate generally, by way of example, but not by way of limitation, various embodiments, and together with the description and claims, serve to explain the disclosed embodiments. When appropriate, the same reference numbers are used throughout the drawings to refer to the same or like parts. Such embodiments are demonstrative and not intended to be exhaustive or exclusive embodiments of the present apparatuses, systems, or methods.

DETAILED DESCRIPTION

In this disclosure, a radiotherapy system and a corresponding method for localizing and tracking a tumor in the anatomy of a patient undergoing radiation therapy treatment are introduced. In particular, during radiation therapy treatment planning a plurality 3D magnetic resonance images (MRI) or 4D MRI images are captured. The exact location of a target, for example, a tumor in the anatomy of the patient can be determined by the radiotherapy system using segmentation techniques, known in the art. After, the location of the tumor is determined, the system can generate a plurality of patches and can determine an offset from a center of the patch to the tumor. A variety of methods, such as correlation or using appearance model techniques, can be used by the radiotherapy system to enhance selected features of the plurality of patches, which result in a plurality of adaptive filter models. These adaptive filter models can then be used by the radiotherapy system during actual "on-line" treatment of a patient.

One advantage of this approach is a target tumor can be localized and tracked during radiotherapy treatment. For a tumor typically moves within the anatomy of the patient because of a variety of types of movement, such as motion caused by respiration, cardiac motion, peristalsis, involuntary motion of the patient, (e.g., a cough, a sneeze, etc.), or voluntary motion caused by the patient being on a treatment table during radiotherapy. When utilizing MRI-guided radiation therapy, only 2D slices of images of the patient's anatomy are available. This approach permits determining which 2D slice(s) include the tumor and further advantageously provides an ability to track the tumor by estimating a potential future location.

Figure 1:
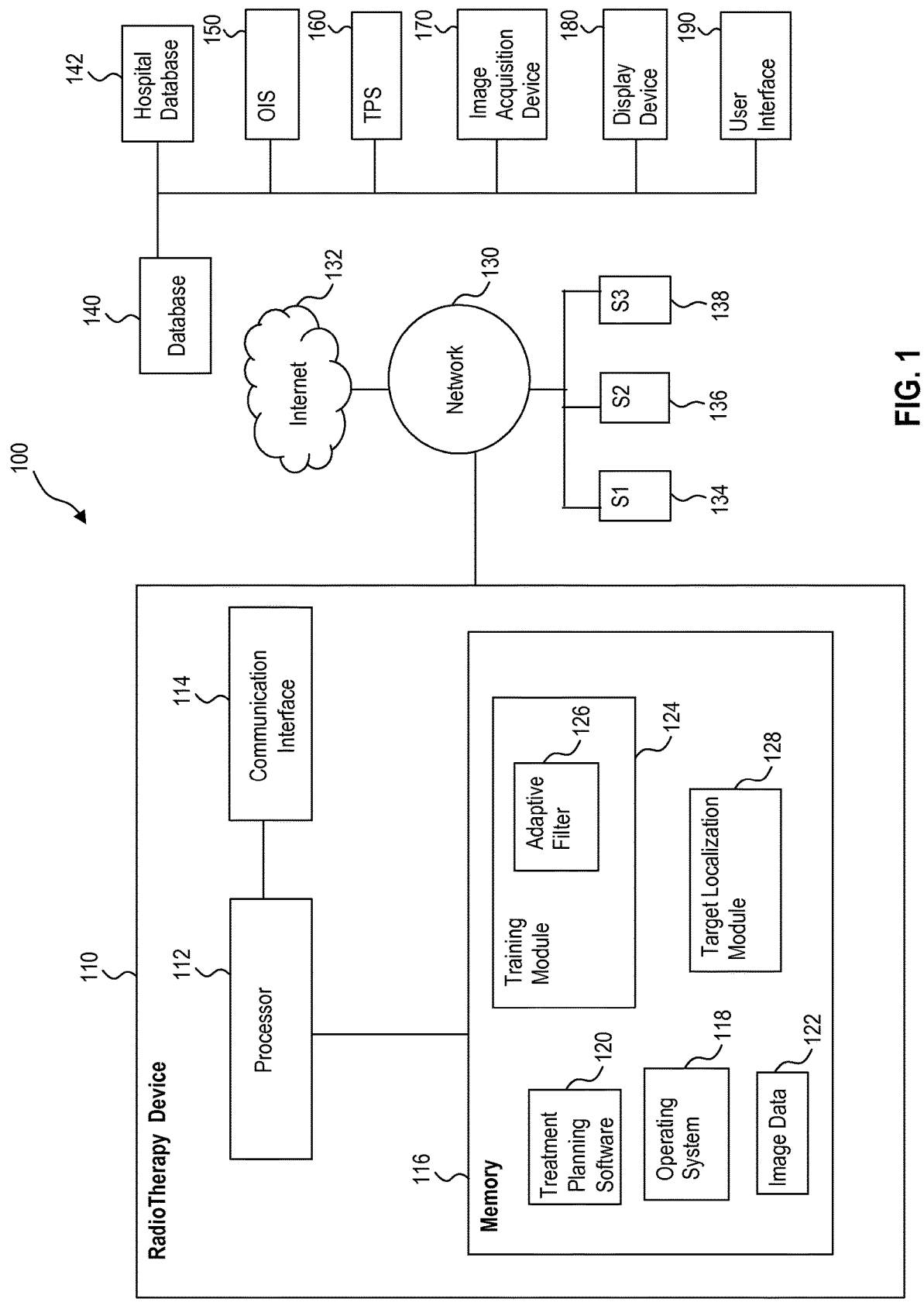
FIG. 1 illustrates an exemplary radiotherapy system to localize and track a three-dimensional target for radiation therapy.

FIG. 1 illustrates an exemplary radiotherapy system 100 for performing target localization and tracking during radiation therapy treatment. Radiotherapy system 100 may include a radiation therapy device 110 connected to a network 120 that is connected to an internet 130. The network 120 can connect the radiation therapy device 110 with a database 140, a hospital database 142, an oncology information system (OIS) 150 (e.g., which may provide patient information), a treatment planning system (TPS) 160 (e.g., for generating radiation therapy treatment plans to be used by the radiotherapy device 110), an image acquisition device 170, a display device 180 and an user interface 190.

The radiotherapy device 110 may include a processor 112, a memory device 116, and a communication interface 114. Memory device 116 may store computer executable instructions, for an operating system 118, treatment planning software 120, a training module 124 that generates an adaptive filter 126, and a target localization module 120 and any other computer executable instructions to be executed by the processor 240.

Processor 112 may be communicatively coupled to the memory device 116, and processor 112 may be configured to execute computer executable instructions stored thereon.

For example, processor 112 may execute training module 124 to implement functionalities of both the training module 124 and functionalities of the target localization module 128 in order to determine a location of the target in a patient during administration of radiotherapy. In addition, processor 112 may execute the treatment planning software 120 (e.g., such as Monaco® software manufactured by Elekta) that may interface with training module 124 and target localization module 128.

The processor 112 may be a processing device, include one or more general-purpose processing devices such as a microprocessor, central processing unit (CPU), graphics processing unit (GPU), an accelerated processing unit (APU), or the like. More particularly, processor 112 may be a complex instruction set computing (CISC) microprocessor, reduced instruction set computing (RISC) microprocessor, very long instruction Word (VLIW) microprocessor, a processor implementing other instruction sets, or processors implementing a combination of instruction sets. Processor 112 may also be one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some embodiments, processor 112 may be a special-purpose processor, rather than a general-purpose processor. Processor 112 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. Processor 112 may also include graphical processing units such as a GPU from the GeForce®, Quadro®, Tesla® family manufactured by Nvidia™, GMA, Iris™ family manufactured by Intel™, or the Radeon™ family manufactured by AMD™. Processor 112 may also include accelerated processing units such as the Desktop A-4(6,8) Series manufactured by AMD™, the Xeon Phi™ family manufactured by Intel™. The disclosed embodiments are not limited to any type of processor(s) otherwise configured to meet the computing demands of identifying, analyzing, maintaining, generating, and/or providing large amounts of imaging data or manipulating such imaging data to localize and track a target or to manipulate any other type of data consistent with the disclosed embodiments. In addition, the term "processor" may include more than one processor, for example, a multi-core design or a plurality of processors each having a multi-core design. Processor 112 can execute sequences of computer program instructions, stored in memory 116, to perform various operations, processes, methods that will be explained in greater detail below.

Memory device 116 can store image data 122 (e.g., 3D MRI, 4D MRI, 2D slices, etc.) received from the image acquisition device 179, or any other type of data/information in any format that the radiotherapy device 110 may use to perform operations consistent with the disclosed embodiments. Memory device 210 may include a read-only memory (ROM), a flash memory, a random access memory (RAM), a dynamic random access memory (DRAM) such as synchronous DRAM (SDRAM) or Rambus DRAM, a static memory (e.g., flash memory, static random access memory), etc., on which computer executable instructions are stored in any format. The computer program instructions can be accessed by the processor 112, read from the ROM, or any other suitable memory location, and loaded into the RAM for execution by the processor 112. For example, memory 116 may store one or more software applications. Software applications stored in memory 116 may include, for example, an operating system 118 for common computer systems as well as for software-controlled devices. Further, memory 116 may store an entire software application or only a part of a software application that is executable by processor 112. For example, memory device 116 may store one or more radiation therapy treatment plans as treatment planning software 120 generated by the treatment planning system 160.

In some embodiments, memory device 116 may include a machine-readable storage medium. While the machine-readable storage medium in an embodiment may be a single medium, the term "machine-readable storage medium" should be taken to include a single medium or multiple media (e.g., a centralized or distributed database, and/or associated caches and servers) that store the one or more sets of computer executable instructions or data. The term "machine-readable storage medium" shall also be taken to include any medium that is capable of storing or encoding a set of instructions for execution by the machine and that cause the machine to perform any one or more of the methodologies of the present disclosure. The term "machine readable storage medium" shall accordingly be taken to include, but not be limited to, solid-state memories, optical and magnetic media. For example, the memory/storage device 210 can be one or more volatile, non-transitory, or non-volatile tangible computer-readable media.

The radiotherapy device 110 can communicate with a network 130 via a communication interface 114, which is communicatively coupled to processor 112 and memory 116. Communication interface 114 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a WiFi adaptor), a telecommunication adaptor (e.g., 3G, 4G/LTE and the like), and the like. Communication interface 114 may include one or more digital and/or analog communication devices that permit radiotherapy device 110 to communicate with other machines and devices, such as remotely located components, via a network 130.

The network 130 may provide the functionality of a local area network (LAN), a wireless network, a cloud computing environment (e.g., software as a service, platform as a service, infrastructure as a service, etc.), a client-server, a wide area network (WAN), and the like. Therefore, network 130 can allow data transmission between the radiotherapy device 110 and a number of various other systems and devices, such as for example: the treatment planning system 160, the Oncology Information System 150, and the image acquisition device 170. Further, data generated by the treatment planning system 160, the OIS 150, and the image acquisition device 170 may be stored in the memory 116, database 140, or hospital databased 142. The data may be transmitted/received via network 130, through communication interface 114 in order to be accessed by the processor 112, as required.

In addition, the network 130 may be connected to the internet 132 to communicate with servers or clients that reside remotely and are connected to the internet. As described, network 130 may include other systems S1 (134), S2 (136), S3 (138). Systems S1, S2, and/or S3 may be identical to system 100 or may be different systems. In some embodiments, one or more systems connected to network 130 may form a distributed computing/simulation environment that collaboratively performs image acquisition, target location and target tracking as well other aspects of providing radiotherapy to a patient.

Additionally, radiotherapy system 100 may communicate with the database 140 or the hospital database 142 in order to execute one or more programs stored remotely. By way of example, database 140, hospital database 142, or both may include relational databases such as Oracle™ databases, Sybase™ databases, or others and may include non-relational databases, such as Hadoop sequence files, HBase, Cassandra, or others. Such remote programs may include, for example, oncology information system (OIS) software or treatment planning software. The OIS software, for instance, may be stored on the hospital database 142, the database 140, or the OIS 150. The treatment planning software, for example, may be stored on the database 140, the hospital database 142, the treatment planning system 160 or the OIS 150. Thus, for instance, radiotherapy device 110 may communicate with the hospital database 142 to implement functionalities of the oncology information system 150.

Systems and methods of disclosed embodiments, however, are not limited to separate databases. In one aspect, radiotherapy system 100 may include database 220 or hospital database 230. Alternatively, database 220 and/or hospital database 230 may be located remotely from the radiotherapy system 100. Database 140 and hospital database 142 may include computing components (e.g., database management system, database server, etc.) configured to receive and process requests for data stored in memory devices of database 140 or hospital database 142 and to provide data from database 220 or hospital database(s) 230. One skilled in the art would appreciate that databases 140, 142 may include a plurality of devices located either in a central or distributed manner.

In addition, radiotherapy device 110 may communicate with database 140 through network 130 to send/receive a plurality of various types of data stored on database 140. For example, in some embodiments, database 140 may be configured to store a plurality of images (e.g., 3D MRI, 4DMRI, 2D MRI slice images, CT images, 2D Fluoroscopy images, X-ray images, raw data from MR scans or CT scans, Digital Imaging and Communications in Medicine (DIMCOM) data, etc.) from image acquisition device 140. Database 140 may store data to be used by the target localization module 128, the training module 124, and the treatment planning software 120. The radiation therapy device 110 may receive the imaging data (e.g., 3DMRI images, 4D MRI images) from the database 120 to order to generate a plurality of adaptive filters models, as described below.

Further, the radiotherapy system 100 can include an image acquisition device 170 that can acquire medical images (e.g., Magnetic Resonance Imaging (MRI) images, 3D MRI, 2D streaming MRI, 4D volumetric MRI, Computed Tomography (CT) images, Cone-Beam CT, Positron Emission Tomography (PET) images, functional MRI images (e.g., fMRI, DCE-MRI and diffusion MRI), X-ray images, fluoroscopic image, ultrasound images, radiotherapy portal images, single-photo emission computed tomography (SPECT) images, and the like) of the patient. Image acquisition device 170 may, for example, be an MRI imaging device, a CT imaging device, a PET imaging device, an ultrasound device, a fluoroscopic device, a SPECT imaging device, or other medical imaging device for obtaining one or more medical images of the patient. Images acquired by the imaging acquisition device 170 can be stored within database 140 as either imaging data and/or test data. By way of example, the images acquired by the imaging acquisition device 170 can be also stored by the radiotherapy device 110 in memory 116.

In an embodiment, for example, the image acquisition device 140 may be integrated with the radiotherapy device 110 as a single apparatus (e.g., a MRI device combined with a linear accelerator, also referred to as a "MRI-Linac" or as an integrated MRI device combined with a Gamma Knife). Such a MRI-Linac can be used, for example, to determine a location of a target organ or a target tumor in the patient, such as to direct radiation therapy according to the radiation therapy treatment plan to a predetermined target.

The image acquisition device 170 can be configured to acquire one or more images of the patient's anatomy for a region of interest (e.g., a target organ, a target tumor or both). Each 2D slice can include one or more parameters (e.g., a 2D slice thickness, an orientation, and a location, etc.). The one or more parameters can be adjusted by using the processor 112, to include the target. For instance, selected features of the 2D slice can be manipulated, e.g., by adjusting the gradient or RF waveform properties. For example, the position of the slice can be varied by changing the basic frequency of the RF pulse and maintaining the same gradient strength. Further, the orientation of the slice can be varied, for example, by using a physically different gradient axis (e.g., the selected slice can be orthogonal to the gradient applied). In an example, the image acquisition device 170 (e.g., an MRI or an MRI-Linac) can acquire a 2D slice in any orientation. For example, an orientation of the 2D slice can include a sagittal orientation, a coronal orientation, or an axial orientation. These orientations can correspond to a magnetic field gradient (e.g., Gx, Gy, or Gz, respectively) associated with the MRI or the MRI-Linac. The processor 112 can adjust a parameter, such as the thickness of the 2D slice, to include the target organ or target tumor. In an example, the thickness of the slice can be calculated and adjusted such as by using Equation 1:

$$T = \frac{2\Delta\omega_s}{\gamma G_{slice}} \quad \text{(Eq. 1)}$$

In Equation 1, T can represent the 2D slice thickness, such as can be measured in units of distance (e.g., millimeters). $\Delta\omega_s$ can represent an excitation bandwidth corresponding to a radio frequency pulse applied at a specified frequency (e.g., Hertz, "Hz"). The letter, $\gamma$, can represent a constant called the gyromagnetic ratio (e.g., for protons, $\gamma$ has a value of 267.54 MHz/Tesla). $G_{slice}$ can represent the magnetic field gradient (e.g., measured in Tesla/meters). In an example, 2D slices can be determined from information such as a 3D MRI volume. Such 2D slices can be acquired by the image acquisition device 170 in "real-time" while a patient is undergoing radiation therapy treatment, for example, when using the radiation therapy device 110.

The treatment planning system 160 may generate and store radiation therapy treatment plans for a particular patient to be treated, radiation therapy treatment plans for other patients, as well as other radiotherapy information (e.g., beam angles, dose-histogram-volume information, the number of radiation beams to be used during therapy, the beam angles, the dose per beam, and the like). For example, treatment planning system 160 may provide information about a particular radiation dose to be applied to the patient and other radiotherapy related information (e.g., type of therapy: such as image guided radiation therapy (IGRT), intensity modulated radiation therapy (IMRT), stereotactic radiotherapy; and the like).

Generating the treatment plan may include communicating with the image acquisition device 170 (e.g., a CT device, a MRI device, a PET device, an X-ray device, an ultrasound device, etc.) in order to access images of the patient and to delineate a target, such as a tumor. In some embodiments, the delineation of one or more organs at risk (OARs), such as healthy tissue surrounding the tumor or in close proximity to the tumor may be required. Therefore, segmentation of the OAR may be performed when the OAR is close to the target tumor. In addition, if the target tumor is close to the OAR (e.g., prostate in near proximity to the bladder and rectum), segmentation of the OAR, the treatment planning system 160 may allow study of the dose distribution not only in the target, but also in the OAR.

In order to delineate a target organ or a target tumor from the OAR, medical images, such as MRI images, CT images, PET images, fMRI images, X-ray images, ultrasound images, radiotherapy portal images, SPECT images and the like, of the patient undergoing radiotherapy may be obtained non-invasively by the image acquisition device 170 to reveal the internal structure of a body part. Based on the information from the medical images, a 3D structure may be obtained. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible), the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker) or automatically (e.g., using a program such as the Atlas-based Auto-segmentation software, ABAS®, manufactured by Elekta, AB, Stockholm, Sweden). In certain embodiments, the 3D structure of a target tumor or an OAR may be generated automatically by the treatment planning system 160.

After the target tumor and the OAR(s) have been located and delineated, a dosimetrist, physician or healthcare worker may determine a dose of radiation to be applied to the target tumor and any OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters, such as volume delineation (e.g., define target volumes, contour sensitive structures), margins around the target tumor and OARs, dose constraints (e.g., full dose to the tumor target and zero dose to any OAR; 95% of dose to PTV, while spinal cord≤45 Gy, brain stem≤55 Gy, and optic structures<54 Gy receive said dosages respectively), beam angle selection, collimator settings, and beam-on times. The result of inverse planning may constitute a radiation therapy treatment plan that may be stored in the treatment planning system 160 or database 140. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the treatment planning system 160 can generate a tailored radiation therapy treatment plan having these parameters in order for the radiotherapy device 110 to provide radiotherapy treatment to the patient.

In addition, the radiotherapy system 100 includes a display device 180 and a user interface 190. The display device 180 may include one or more display screens that display medical images, interface information, treatment planning parameters (e.g., contours, dosages, beam angles, etc.) treatment plans, a target, localizing a target and/or tracking a target, or any related information to the user. The user interface 190 may be a keyboard, a keypad, a touch screen or any type of device that a user may input information to radiotherapy system 100.

In order for the radiation therapy device 110 to localize and track a target tumor in an anatomical region of interest, for example, processor 112 can execute the target localization module 128. The target acquisition module 120 may utilize the adaptive filter model 126 generated by the training module 124, as described later in this disclosure. Further, the adaptive filter model can include particular domain information (e.g., a spatial domain or a frequency domain), location information (e.g., 3D location in a volume, 3D offset information, or 2D displacement information). The target localization module 128 uses at least one adaptive filter model 126 generated by a training module 124, as described below.

Furthermore, any and all components of the radiotherapy system 100, in an embodiment, may be implemented as a virtual machine (e.g., VMWare, Hyper-V, and the like). For instance, a virtual machine can be software that functions as hardware. Therefore, a virtual machine can include at least one or more virtual processors, one or more virtual memories, and one or more virtual communication interfaces that together function as hardware. For example, the OIS 150, the TPS 160, the image acquisition device 170 could be implemented as a virtual machine. Given the processing power, memory, and computational capability available, the entire radiotherapy system could be implemented as a virtual machine.

Figure 2:
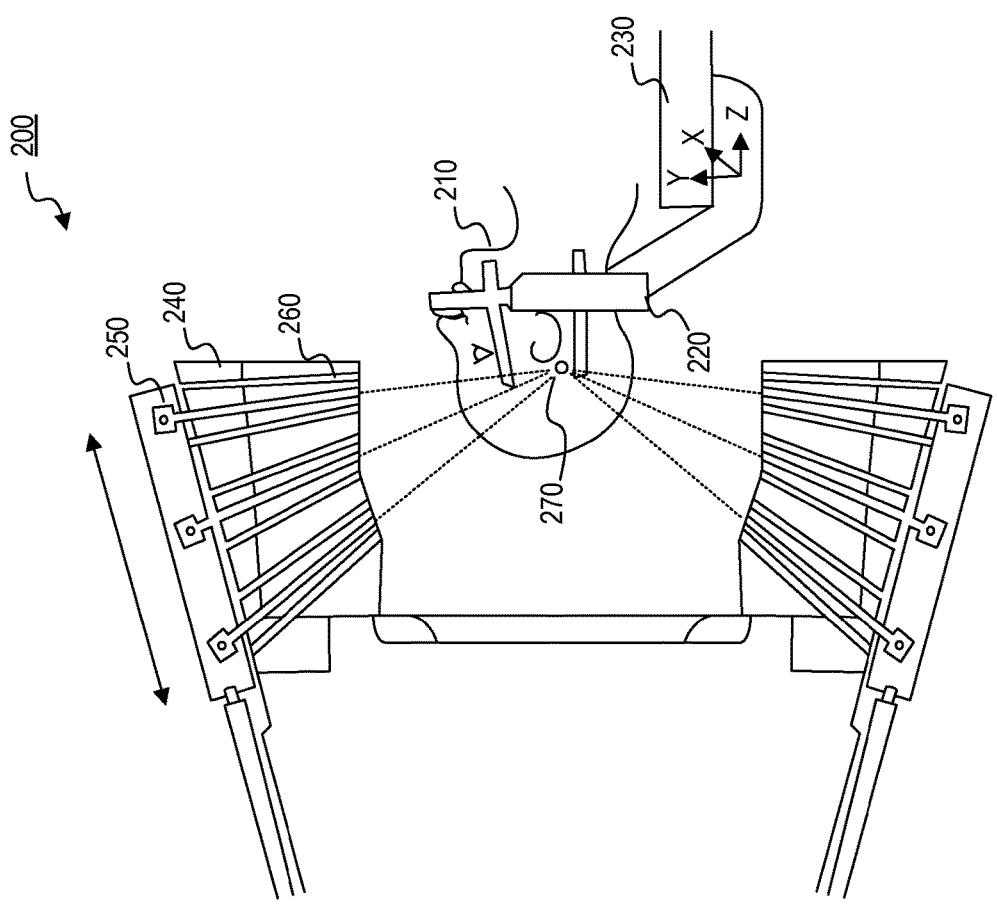
FIG. 2 illustrates a radiotherapy device, a Gamma Knife, used in the radiotherapy system of FIG. 1.

FIG. 2 illustrates an example of one type of radiation therapy treatment device 200, for example, a Leksell Gamma Knife, manufactured by Elekta, AB, Stockholm, Sweden. The Gamma Knife can be configured to utilize the target localization module 128 (shown in FIG. 1), which may remotely access MRI images (e.g., from the image acquisition device 170) to localize a target tumor in the brain. In an embodiment, an MRI apparatus, as an image acquisition device 170, can be integrated with the Gamma Knife. As shown in FIG. 2, during a radiotherapy treatment session, a patient 210 may wear a coordinate frame 220 to keep stable the patient's body part (e.g., the head) undergoing surgery or radiotherapy. Coordinate frame 220 and a patient positioning system 230 may establish a spatial coordinate system, which may be used while imaging a patient or during radiation surgery. Radiotherapy device 200 may include a protective housing 240 to enclose a plurality of radiation sources 250. Radiation sources 250 may generate a plurality of radiation beams (e.g., beamlets) through beam channels 260. The plurality of radiation beams may be configured to focus on an isocenter 270 from different directions. While each individual radiation beam may have a relatively low intensity, isocenter 270 may receive a relatively high level of radiation when multiple doses from different radiation beams accumulate at isocenter 270. In certain embodiments, isocenter 270 may correspond to a target under surgery or treatment, such as a tumor.

Figure 3:
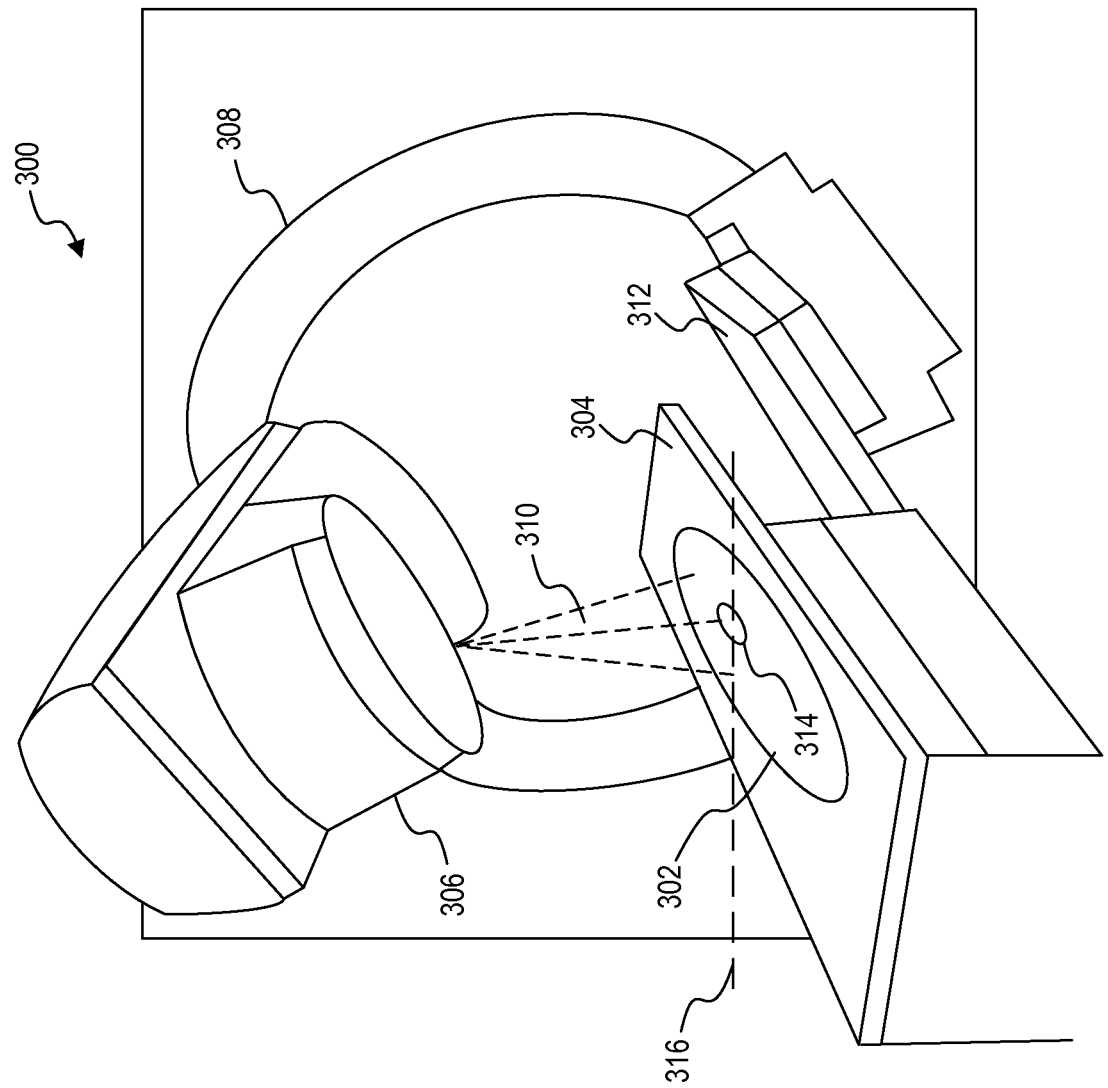
FIG. 3 illustrates a radiotherapy device, a linear accelerator, used in the radiotherapy system of FIG. 1.

FIG. 3 illustrates another example of a type of radiation therapy device 300 (e.g., a linear accelerator, referred to as a LINAC, manufactured by Elekta, AB, Stockholm, Sweden). Using the linear accelerator 300, a patient 302 may be positioned on a patient table 304 to receive the radiation dose determined by a radiation therapy treatment plan generated by the treatment planning system 160 (shown in FIG. 1). The radiation treatment plan can be used to localize and track a 3D target in a volume, such as a target organ or a target tumor located within the anatomy of the patient 302.

The linear accelerator 300 may include a radiation head 306 connected to a gantry 308 that rotates around the patient 302. The radiation head 306 generates a radiation beam 310 that is directed toward the target organ or target tumor. As the gantry 308 rotates, the radiation head 306 can rotate around the patient 302. While rotating, the radiation head 306 may provide patient 302 with a plurality of varying dosages of radiation depending upon the angle and the shape and size of the tumor according to the treatment plan generated by the treatment planning system 160 (shown in FIG. 1). Because organs and tumors move within a patient's body, fast and accurate 3D localization of the target is important. For instance, a target organ or tumor may move because of various types of motion (e.g., respiratory, cardiac, peristalsis or other types of patient motion). Therefore, the linear accelerator 300 may be configured to localize the target (e.g., organ or tumor) and track the target during radiation therapy treatment by using target localization module 128.

In addition, below the patient table 304, a flat panel scintillator detector 312 may be provided, which may rotate synchronously with the radiation head 306 around an isocenter 314 located on a target organ or a target tumor on the body of the patient 32. The flat panel scintillator can acquire images with the highest achievable signal-to-noise ratio and can be used for verification of the amount of radiation received by the patient 302 during any particular radiation therapy treatment session (e.g., a radiation therapy treatment may require multiple sessions of radiation therapy, where each session is typically referred to as a 'fraction'). Further, such images are used to determine the geometric accuracy of patient positioning relative to the radiation head 306.

The intersection of an axis 316 with the center of the beam 310, produced by the radiation head 306, is usually referred to as the "isocenter". The patient table 304 may be motorized so the patient 302 can be positioned with the tumor site at or close to the isocenter 314. For instance, the patient table 304 may change positions relative to one or more other components of the linear accelerator 300, such as to elevate, change the longitudinal position, or the latitudinal position of the patient 302 relative to a therapeutic radiation source located in the radiation head 306.

In an embodiment the linear accelerator 300 may be integrated with the image acquisition device 170 (shown in FIG. 1), such as a magnetic resonance imaging device as a single apparatus (e.g., a MRI-Linac). In such a case, the MRI-Linac may include a "virtual couch" that can "virtually" adjust the alignment of the patient 302 relative to the radiation source when the patient table 304 is configured not to move because of the limited dimensions of a bore size through which the patient table 304 is inserted during radiation therapy treatment. In such an embodiment the MRI-Linac can be used to determine a location of the target and track the target in the patient 302 using the target localization module 128, such as to direct radiation therapy to a predetermined target.

Figure 4:
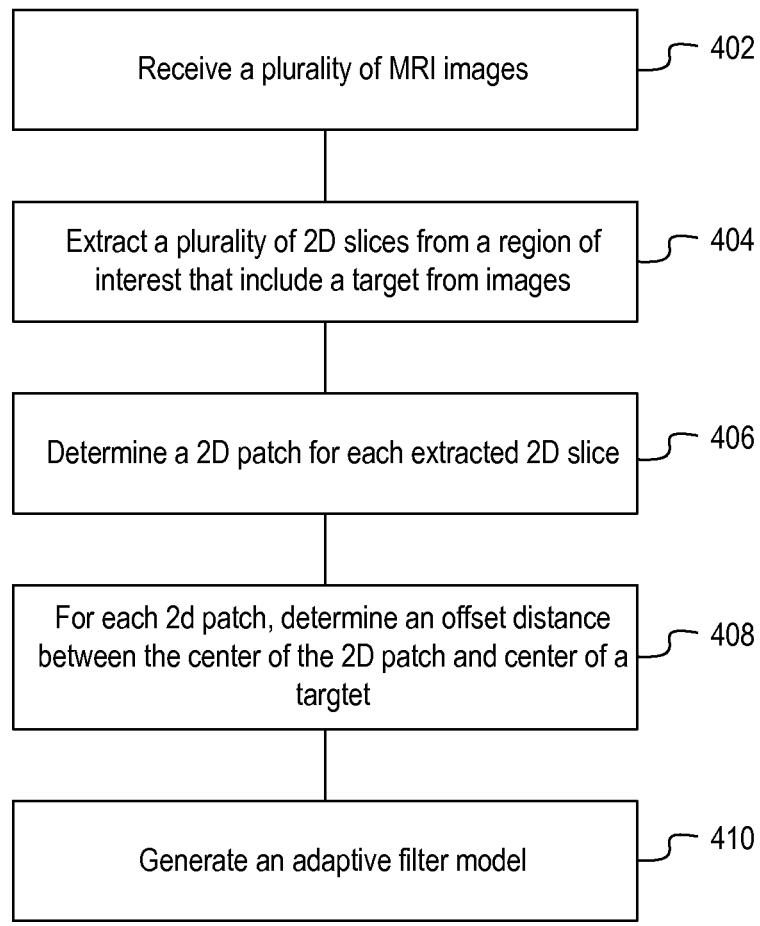
FIG. 4 illustrates an exemplary flowchart for a training module to generate an adaptive filter model.

FIG. 4 illustrates a process 400 for the training module 124 to generate an adaptive filter model 126. The adaptive filter model 126 (shown in FIG. 1) can be utilized by the target localization module 128 to determine a location of a target and then track the target.

At 402, the training module 124 (shown in FIG. 1) receives a plurality of images (e.g., 3D MRI, 4D MRI etc.) from the image acquisition device 170 of a region of interest for a particular patient. The plurality of images, for example, can be 3D MRI images or 4D MRI images of a region of interest that contain a target (e.g., a target organ, target tumor, etc.).

At 404, the training module 110 using processor 112 proceeds to extract a plurality of slices (e.g., 2D slices) that include the target (e.g., target organ, target tumor, etc.) in the region of interest from the plurality if MRI images. The thickness, for example, of the 2D slices can be predetermined (e.g., determined from information based on the 3D MRI volume or the 4D MRI volume) prior to beginning radiation therapy treatment. The information may include whether the 2D slices should be in a frequency domain or a spatial domain. Alternatively, the training module 110 may receive 2D slice information when the patient 402 is being treated with radiation therapy (e.g., in real-time). For example, an MRI-Linac could be used to treat the patient 402 with radiation therapy. During this process of radiotherapy, the MRI-Linac can take a plurality of 3DMRI images or 4DMRI images during the treatment process. The extracted slices represent 2D slices of the anatomy of the patient that surrounds the target. Further, the extracted 2D slices may be either parallel or orthogonal to the motion of the target.

At 406, the processor 112 determines one or more 2D patches for each extracted 2D slice. In an example, a 2D patch can correspond to an area of the 2D slice image that can include the target. The 2D patch can be configured in any shape (e.g., a square, a rectangle, a circle, a polygon shape, etc.) and can vary in size (e.g., a 32×32 pixel patch, a 64×64 pixel patch, etc.). For illustration, a square patch, for example, can be 32×32 pixels corresponding to the target in a 2D slice that is 512×512 pixels. In an example, the 2D patch can include information about the target and information corresponding to an area that does not include the target (e.g., background information).

At 408, the processor 112 determines an offset value. The offset value is, for example, a distance from a center of the 2D patch to a center of the target that is to be tracked. The 2D patches can include domain information (e.g., information about a spatial domain or frequency domain of the 2D patches). Further, the offset information can include information such as the displacement of the 2D patch from a reference point (e.g., a reference point corresponding to the target in the volume), and information about a change in shape of the target (e.g., deformation). In an example, the reference point can include a calculated center of the target (e.g., a tumor centroid). An offset value is determined for each 2D patch containing the target. Therefore, each 2D patch has its own associated offset value. The plurality of offset values and their associated patches are stored in memory 116.

For instance suppose the center of the 2D patch has coordinates (e.g., [xp, yp, zp]) and the center of the target tumor has coordinates (e.g., [xt, yt, zt]) then the offset of the 2D patch center related to the 3D location of the target tumor can be a vector (e.g., [ox, oy, oz]=[xt−xp, yt−yp, zt−zp]). Therefore, the processor 112 can track the target tumor. During tracking, the processor 112 can locate the center of the 2D patch for a new patient setup (e.g., "on-line/real-time" as, for example [xpnew, ypnew, zpnew]). The processor 112 can then determine the location of the tumor (e.g., [xtnew, ytnew, ztnew]=[xpnew+ox, ypnew+oy, zpnew+oz]).

At 410, the processor 112 can use one or more types of adaptive filter design techniques to convert each of the patches into an adaptive filter model 126. For example, the following types of adaptive filter designs may be used: matched filters, maximum margin correlation filters, synthetic discriminant function filters, least mean square filters, and the like. Furthermore, the adaptive filter model 126 can include the domain information and offset information as determined from the 2D patches corresponding to the target in the volume.

In general, the adaptive filter models 126, for example, "model" an object (e.g., a tumor) to be located. A plurality of adaptive filter models 126 can be generated. For example, there can be an adaptive filter model 126 for the top of the tumor, an adaptive filter model 126 for the middle of the tumor, and an adaptive filter model 126 for the bottom of the tumor. In addition, adaptive filter models 126 can be created for various parts of the human anatomy (e.g., one or more target organs of interest, such as prostate, breast, lung, heart, brain, etc.). In addition, adaptive filter model 126 can be generated for each target of interest (e.g., one or more tumors in a particular organ—such as multiple tumors in a lung; or in the case where cancer has metastasized and there are one or more tumors in one or more organs, etc.).

Furthermore, the adaptive filter model 126 may be designed in either a spatial domain or in a frequency domain. In an example, the application of the adaptive filter model 126 to the 2D slices can be more computationally efficient in the frequency domain. The adaptive filter model 126 can be stored in memory 116 (shown in FIG. 1) and retrieved by processor 112 to be applied to subsequently acquired 2D slices (e.g., 2D slices acquired in "real-time"/"on-line") to predict the location of the target during radiation therapy treatment of the patient.

Figure 5:
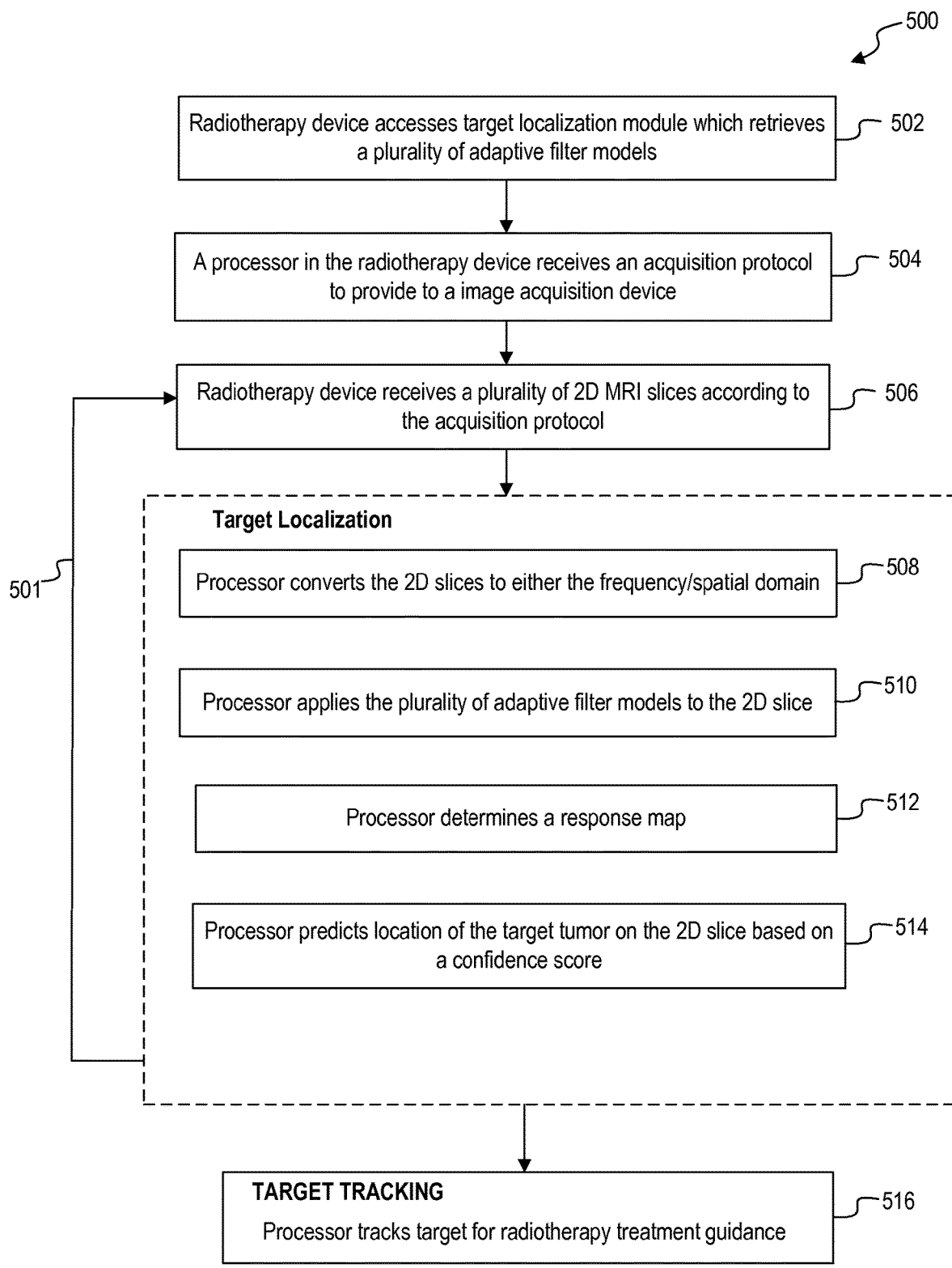
FIG. 5 illustrates an exemplary flowchart for using one or more trained adaptive filter models to localize and track a tumor during radiation treatment of a patient.

FIG. 5 illustrates an exemplary flowchart for a workflow process 500 for using one or more adaptive filter models 126 to track a target during "real-time"/"on-line" radiation therapy treatment of the patient.

At 502, the process 500 begins by the radiotherapy device 10 (shown in FIG. 1) using processor 116 accesses the target localization module 128 which retrieves a plurality adaptive filter models 126 designed for a region of interest (e.g., prostate, breast, lungs, etc.) including the target tumor for a particular patient.

At 504, the processor 116 receives an acquisition protocol to provide to the image acquisition device 170 to generate an initial set of 2D slices. The protocol may include, for example, a location of slices to be taken (e.g., lung, prostate, brain, kidney, etc.), an orientation of the slice (e.g., based on a predetermined potential organ motion—such as parallel or orthogonal to the slice to be taken), and a slice thickness (e.g., a 5 mm slice, a 10 mm slice, a 15 mm slice, etc.). A user may provide an initial estimate of the location of the target, which can be provided through the user interface 190. The processor 116 can utilize this initial estimate as an initial location of where to begin taking 2D slices. Alternatively, such location information can be determined automatically by processor 116.

At 506, the radiotherapy device further receives a plurality of 2D MRI slices according to the protocol from the image acquisition device 170 (e.g., a MRI device or a MRI-Linac device). The 2D images can correspond to the region of interest having the tumor. The 2D slices may be parallel or orthogonal to the tumor. The 2D slices may surround the tumor. Further, the 2D slices may be the region around the tumor. Typically, an MRI device provides 2D slices in the frequency domain.

At 508 through 514, described below, the processor 116 determines the location of a tumor on a 2D slice and its location in a 3D volume.

At 508, the processor 116 can convert the 2D slices to either the frequency domain or the spatial domain. The 2D slices are converted to match the domain of the adaptive filter model 126. For example, if the adaptive filter model 126 was created in the spatial domain, the 2D slices, for example, the processor 116 may convert the 2D slices to the spatial domain. Alternatively, if the adaptive filter model 126 was created in the frequency domain, the processor 116 may convert the 2D slices to the frequency domain.

At, 510, the processor 116 can apply the adaptive filter model 126. As discussed above the adaptive filter model 126 is a plurality of models generated from a plurality of 2D patches that have been trained by the training module 126. The processor 112 applies the plurality of adaptive filter models 126 to the 2D slices. The 2D slice and the adaptive filter model, for example, can have the same orientation (e.g., orthogonal to the direction of motion, parallel to the direction of motion, or both). In an example, the application of the adaptive filter model 126 to the 2D slices can be more computationally efficient in the frequency domain. An example of how the adaptive filter model 126 can be applied to the 2D slices e follows:

The adaptive filter model 126 can be denoted by a 2D template T(x, y) in the spatial domain, and a 2D slice (e.g., a 2D image) can be denoted by I(x, y). Applying the adaptive filter model 126 to a particular location of the 2D slice can provide a correlation-related "confidence score". The confidence score, for example, provides an indication of how well the particular adaptive filter model matches a particular location of the 2D slice.

In an example, the better the match the adaptive filter model 126 has relative to a particular location of the 2D slice, the higher the confidence score. The confidence score can be used to predict whether and where the target tumor is located within the 2D slice. A number of various types of correlation can be utilized to determine the confidence score depending on the circumstances. For example, the following types of correlation may be used: cross-correlation, normalized cross-correlation, or correlation coefficient, which can be defined as follows:

Cross-correlation: $R(x,y) = \Sigma_{i,j \in P} T(i,j) \cdot I(x-i, y-j)$;

Normalized cross-correlation: $N(x, y) =$ $$\frac{\sum_{i,j \in P} T(i, j) \cdot I(x-i, y-j)}{\sqrt{\sum_{i,j \in P} T(i, j)^2} \sqrt{\sum_{i,j \in P} I(x-i, y-j)^2}};$$

Correlation coefficient $C(x, y) =$ $$\frac{\sum_{i,j \in P}(T(i,j) - \bar{T}) \cdot (I(x-i, y-j) - \bar{I})}{\sqrt{\sum_{i,j \in P}(T(i,j) - \bar{T})^2} \sqrt{\sum_{i,j \in P}(I(x-i, y-j) - \bar{I})^2}}$$

(e.g., the correlation coefficient is equivalent to the normalized cross-correlation of the mean-corrected template and image).

In the above equations: P denotes the spatial domain of the template; $\bar{T}$ and $\bar{I}$ denote the mean value of the template T and the slice I, respectively. Further, both N(x, y) and C(x, y) are bounded, for example, by $-1 \leq N(x, y), C(x, y) \ll +1$, such that their values can be interpreted as a confidence score relative to the perfect match result of +1. The confidence score can include information such as, for example, R, N, or C as defined above.

The three correlation computations can also be performed in the frequency domain by applying the convolution theorem, for example: $R = \mathcal{F}^{-1}\{\mathcal{F}\{T\} \cdot \mathcal{F}\{I\}\}$, where $\mathcal{F}\{\ \}$ and $\mathcal{F}^{-1}\{\ \}$ denote the forward and inverse Fourier transform respectively.

At 512, the processor 112 can determine a response map, as a result of the application of an adaptive filter model 126 to the 2D slice. A plurality of response maps can be created for a single 2D slice, for each response map can correspond to a particular adaptive filter model. Both the adaptive filter model and the 2D slice can have the same orientation. The response map may be generated in a spatial domain or a frequency domain. Both the 2D slice and the adaptive filter model 126 have to be in the spatial domain to generate a response map in the spatial domain. Similarly, both the 2D slice and the adaptive filter model 126 have to be in the frequency domain to generate a response map in the frequency domain. A response map can be created for every 2D slice. The generated response map can be an image that indicates the degree a particular adaptive filter model 126 matches various locations within a given 2D slice.

For example, an adaptive filter model A (not shown) can be applied by the processor 112 to every location on a 2D slice. For each location, the processor 112 can determine a confidence score that indicates how well, for instance, the adaptive filter A matches a particular location of the 2D slice. The better the match is between the adaptive filter model A relative to the location on the 2D slice, the higher the confidence score (e.g., closer to +1) for that particular location. Brighter areas on the response map image can indicate a better match, and therefore, a higher confidence score (e.g., between the adaptive filter model A at the particular location of the 2D slice) than darker areas. Brighter areas can have higher confidence scores than darker areas in the response map. After, the adaptive filter model A is applied to the 2D slice, a response map A can be generated. The processor 112 can retrieve another adaptive filter model B (not shown), for example, and repeat the process of applying the adaptive filter model B to every location on the 2D slice to generate a response map B. Thus, the processor using the target localization module can apply a plurality of adaptive filter models to the 2D slice to generate a plurality of response maps, which can be stored in memory 116. At each location of the 2D slice, a confidence score is generated corresponding to the adaptive filter model utilized. A high confidence score may correspond to a location on the 2D slice where the target tumor may be located.

At 514, the processor 112 can predict the target tumor location on the 2D slice based on the confidence score. For example, for a particular location on the response map, there can be multiple confidence score values, where each confidence score can correspond to a particular adaptive filter model. In order to predict the tumor's location, the processor 112 can select the maximum confidence score value for a particular location on the 2D slice. Alternatively, the processor 112 can use a weighted average of all the confidence scores for a particular location on the 2D slice. In an example, the processor 112 may compute the weighted average of the top N confidence scores, where N is a predetermined number. Using the confidence scores generated by using multiple adaptive filter models can increase the accuracy of the prediction. Therefore, a high confidence score for a particular location can indicate the location of the target on the 2D slice, and a low confidence score can indicate the tumor is not at that location. A confidence score closest to +1 can indicate that a part of the tumor or the whole tumor is located on the 2D slice.

If processor 112 determines that the 2D slice does not contain a tumor, the process 500 follows 501 to return to 506 to acquire another 2D slice. The process 500 may cause the processor 112 to adjust the acquisition protocol in order to acquire the next 2D slice. Alternatively, the tumor may be included in one or more 2D slices depending on slice thickness, the size of the tumor, the orientation of the tumor and other factors. For example, if the bottom of the tumor is included in the present 2D slice, the processor 112 may use offset information to determine what 2D slice should subsequently be acquired (e.g., a 2D slice containing the centroid of the tumor or may be a 2D slice including the top of the tumor).

For example, using information from a particular adaptive filter model and its corresponding response map, the processor 112 can determine the location of the tumor on previous 2D slice. Further, using offset information associated with the adaptive filter model, the processor 112 can also estimate a location (e.g., the center) of the tumor in 3D. For example, the processor 112 may determine that the tumor intersects the 2D slice at, for example, the (5,10)-th pixel location and the center of the tumor can be 5 mm from the center of the 2D slice in the slice normal direction. In order to estimate the next position of the tumor (e.g., track the tumor as it moves) or to acquire more complete information about the shape of the tumor (e.g., whether the shape of the tumor has changed) the processor 112 can adjust various parameters (e.g., a location where a subsequent 2D slice will be acquired, acquiring a subsequent 2D slice that is parallel to the previous slice but in a different position, acquiring a 2D slice that is orthogonal to the previous slice, adjusting the thickness of the subsequent slice, etc.). Further, using offset information from the previous adaptive filter model, the processor 112 can also estimate the next position of the tumor. Thus, the processor 112 can track the movement of the tumor in real-time as a patient undergoes radiation therapy.

At 516, the processor 112 can track the tumor as the patient undergoes in "real-time" radiation therapy treatment. In addition, the processor 112 can estimate the shape of the tumor when multiple 2D slices are utilized.

Figure 6:
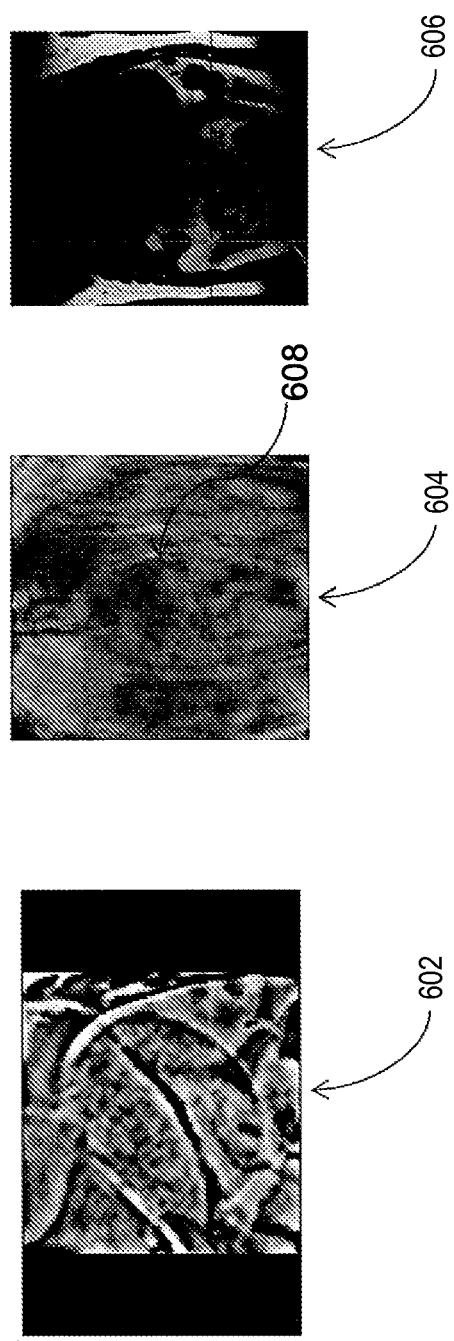
FIG. 6 is a pictorial illustration of an adaptive filter model, a response map, and an image of tracking a target in a patient.

FIG. 6 pictorially illustrates an exemplary adaptive filter model applied to a 2D MRI slice to determine a location of a target (e.g., a liver). At 602, an example of an adaptive filter model in the spatial domain is pictorially represented. The processor 112 (shown in FIG. 1) can use the target localization module 129 to apply the adaptive filter model shown in 602 to a particular 2D slice, which is also in the spatial domain. By applying the exemplary adaptive filter model 602 to the 2D slice, the processor 112 can determine for each location of the 2D slice how well the exemplary adaptive filter model 602 matches a particular location of the 2D slice. Advantageously, the processor 112 can compute each 2D slice in approximately 300 ms. The target localization module 129 generates an exemplary response map, which is pictorially illustrated in 604. The exemplary response map 604 can represent how well the adaptive filter model 602 matched each location of the 2D slice. Brighter areas shown in the exemplary response map 604 indicate a better match, and therefore, a higher confidence score, between the adaptive filter model 602 at the particular location of the 2D slice than darker areas. Brighter areas can have higher confidence scores than darker areas in the response map 604. As illustrated, the response map 604 indicates a bright area 608 that can correspond to the highest confidence score for this 2D slice, as determined by processor 112. The bright area 608 on the response map 604, therefore, can correspond to a location of a target on this particular 2D slice. Therefore, the processor 112 has determined the location of the target 608 that is located on this particular 2D slice. Further, because the location of the patient's anatomy from where the 2D slice was generated by the image acquisition device 170, the processor 112 can determine the location of the target 608, on the patient's anatomy as shown in 606. The red area in 606 corresponds, for example, to the adaptive filter model 602 overlayed on the patient's anatomy. In another embodiment, for example, the target can represent a tumor.

Alternatively, a response map, for example, can be represented in the frequency domain depending on if the 2D slices and the adaptive filter model are in the frequency domain. To generate a response map in the frequency domain, processor 112 can perform a fast-fourier transform (FFT) on the 2D slice. The processor 112 applies the adaptive filter model, by performing a point-by-point multiplication in the frequency domain. To generate the response map, the processor 112 can perform an inverse-fast-fourier transform.

Additional Notes

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

The exemplary disclosed embodiments describe systems and methods for tracking a target (e.g., a tumor) in the anatomy of a patient, while the patient undergoes radiation therapy treatment. The foregoing description has been presented for purposes of illustration. It is not exhaustive and is not limited to the precise forms or embodiments disclosed. Modifications and adaptations of the embodiments will be apparent from consideration of the specification and practice of the disclosed embodiments.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, an apparatus, system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include software code, such as microcode, assembly language code, a higher-level language code, or the like. The various programs or program modules can be created using a variety of software programming techniques. For example, program sections or program modules can be designed in or by means of Java, Python, C, C++, assembly language, or any known programming languages. One or more of such software sections or modules can be integrated into a computer system and/or computer-readable media. Such software code can include computer readable instructions for performing various methods. The software code may form portions of computer program products or computer program modules. Further, in an example, the software code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods can be modified in any manner, including by reordering steps or inserting or deleting steps. It is intended, therefore, that the specification and examples be considered as example only, with a true scope and spirit being indicated by the following claims and their full scope of equivalents.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed:

1. A computer-implemented method for generating a model to track a three-dimensional (3D) target in a region of interest in a patient, the method comprising:
   receiving, by a processor, a 3D medical image;
   extracting a two-dimensional (2D) slice that includes the target from the 3D medical image;
   determining one or more 2D patches from the 2D slice;
   computing, for the one or more 2D patches, an offset from a center of a respective one of the one or more 2D patches to a center of the target, the offset comprising a vector that is computed as a function of a 3D coordinate of the respective one of the one or more 2D patches to a 3D location of the target; and
   generating the model based on the one or more 2D patches and the offset computed for the one or more 2D patches.

2. The method of claim 1, wherein the 2D slice is based on a direction of motion with respect to the target in the patient, the offset being stored in association with the respective one of the one or more 2D patches to indicate a location of the respective one of the one or more 2D patches relative to the target.

3. The method of claim 1 further comprising determining a correlation between the model and the 2D slice, wherein a given one of the one or more 2D patches is of a circular shape.

4. The method of claim 1, wherein the model is used to estimate a 3D location of the target within the patient, wherein a given one of the one or more 2D patches includes domain information about a frequency domain of the given one of the one or more 2D patches, and wherein the given one of the one or more 2D patches includes information about a change in shape of the target.

5. The method of claim 1, wherein the 2D slice includes at least one of a target location parameter, a slice orientation parameter, or a slice thickness parameter.

6. The method of claim 1, wherein the 2D slice is orthogonal to motion of the target, further comprising computing a first vector corresponding to a first offset for a first 2D patch of the one or more 2D patches, the first vector comprising: a first coordinate computed based on a difference between coordinates of the first 2D patch and the 3D location along a first axis, a second coordinate computed based on a difference between coordinates of the first 2D patch and the 3D location along a second axis, and a third coordinate computed based on a difference between coordinates of the first 2D patch and the 3D location along a third axis.

7. The method of claim 1, wherein the 2D slice is received from an image acquisition device based on a frequency of a radio frequency (RF) pulse and a gradient strength of the RF pulse.

8. The method of claim 7, wherein a position of the 2D slice received from the image acquisition device varied by changing the frequency of the RF pulse and maintaining the same gradient strength.

9. The method of claim 1 further comprising generating a response map comprising a confidence score for a location on the 2D slice, wherein the confidence score indicates a degree of correlation between the model and the location on the 2D slice.

10. The method of claim 9, further comprising generating a plurality of response maps for the 2D slice, wherein a response map corresponds to an individualized model.

11. The method of claim 10, further comprising calculating a weighted average of the confidence scores from the plurality of response maps for a particular location on the 2D slice.

12. The method of claim 11, wherein a higher weighted average of confidence scores indicates a higher degree of correlation between the model and the location on the 2D slice.

13. The method of claim 11, wherein the weighted average of confidence scores provides a prediction of the location of the target on the 2D slice.

14. The method of claim 1 further comprising:
   receiving, from an image acquisition device, a plurality of 2D slices of the region of interest;
   contouring the target within individual 2D slices;
   combining a plurality of contours associated with the corresponding plurality of 2D slices; and
   generating a 3D structure of the target based on the combined plurality of contours.

15. A system comprising:
   a memory storing computer-executable instructions; and
   a processor executing the instructions to perform operations comprising:
   receiving a 3D medical image;
   extracting a two-dimensional (2D) slice that includes a target from the 3D medical image;
   determining one or more 2D patches from the 2D slice;
   computing, the one or more 2D patches, an offset from a center of a respective one of the one or more 2D patches to a center of the target, the offset comprising a vector that is computed as a function of a 3D coordinate of the respective one of the one or more 2D patches to a 3D location of the target; and
   generating a model based on the one or more 2D patches and the offset computed for the one or more 2D patches.

16. The system of claim 15, wherein the 2D slice is based on a direction of motion with respect to the target in a patient, the offset being stored in association with the respective one of the one or more 2D patches to indicate a location of the respective one of the one or more 2D patches relative to the target.

17. The system of claim 15, wherein the operations further comprise determining a correlation between the model and the 2D slice, wherein a given one of the one or more 2D patches is of a circular shape.

18. The system of claim 15, wherein the model is used to estimate a 3D location of the target within a patient, wherein a given one of the one or more 2D patches includes domain information about a frequency domain of the given one of the one or more 2D patches, and wherein the given one of the one or more 2D patches includes information about a change in shape of the target.

19. The system of claim 15, wherein the 2D slice includes at least one of a target location parameter, a slice orientation parameter, or a slice thickness parameter.

20. The system of claim 15, wherein the 2D slice is either parallel or orthogonal to motion of the target, further comprising operations for computing a first vector corresponding to a first offset for a first 2D patch of the one or more 2D patches, the first vector comprising: a first coordinate computed based on a difference between coordinates of the first 2D patch and the 3D location along a first axis, a second coordinate computed based on a difference between coordinates of the first 2D patch and the 3D location along a second axis, and a third coordinate computed based on a difference between coordinates of the first 2D patch and the 3D location along a third axis.

\* \* \* \* \*